(12) United States Patent
Kinoshita et al.

(10) Patent No.: US 8,088,123 B2
(45) Date of Patent: Jan. 3, 2012

(54) HAIR GROWTH MODULATION DEVICE

(75) Inventors: Masato Kinoshita, Hikone (JP); Chosei Hamada, Kadoma (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 81 days.

(21) Appl. No.: 12/524,566

(22) PCT Filed: Jan. 24, 2008

(86) PCT No.: PCT/JP2008/050983
§ 371 (c)(1),
(2), (4) Date: Jul. 24, 2009

(87) PCT Pub. No.: WO2008/090952
PCT Pub. Date: Jul. 31, 2008

(65) Prior Publication Data
US 2010/0010507 A1    Jan. 14, 2010

(30) Foreign Application Priority Data

Jan. 26, 2007    (JP) .................................. 2007-017101
Jan. 26, 2007    (JP) .................................. 2007-017102

(51) Int. Cl.
*A61B 18/18*    (2006.01)
(52) U.S. Cl. ............................................. 606/9; 607/88
(58) Field of Classification Search ................... 128/898; 606/2–19; 607/88–94
See application file for complete search history.

(56) References Cited

U.S. PATENT DOCUMENTS

| 5,065,515 | A | 11/1991 | Iderosa |
| 5,802,721 | A | 9/1998 | Wain et al. |
| 6,187,001 | B1 | 2/2001 | Azar et al. |
| 6,233,829 | B1 | 5/2001 | Oglesby et al. |
| 6,511,475 | B1 | 1/2003 | Altshuler et al. |
| 6,533,775 | B1* | 3/2003 | Rizoiu ................ 606/9 |
| 7,479,137 | B2* | 1/2009 | Yamazaki et al. ........ 606/9 |
| 2002/0014011 | A1 | 2/2002 | De Vries et al. |
| 2003/0032950 | A1 | 2/2003 | Altshuler et al. |
| 2005/0177139 | A1 | 8/2005 | Yamazaki et al. |
| 2006/0173447 | A1* | 8/2006 | Jay ........................ 606/9 |
| 2006/0189964 | A1 | 8/2006 | Anderson et al. |
| 2006/0259102 | A1 | 11/2006 | Slatkine |
| 2007/0173746 | A1 | 7/2007 | Barzilay et al. |
| 2008/0215038 | A1* | 9/2008 | Bakker et al. ............ 606/9 |
| 2008/0319429 | A1* | 12/2008 | Van Hal et al. .......... 606/9 |

FOREIGN PATENT DOCUMENTS

JP    2001-37534 A    2/2001
(Continued)

OTHER PUBLICATIONS

Supplementary European Search Report for the Application No. EP 08 70 3810 dated Sep. 24, 2010.

(Continued)

*Primary Examiner* — Henry M Johnson, III
(74) *Attorney, Agent, or Firm* — Cheng Law Group, PLLC

(57) ABSTRACT

A hair growth modulation device is configured to impart a suitable quantity of irradiated light to a target site while lowering the irradiation intensity required by a light irradiator that generates modulating light for modulating hair growth. This device is provided with a hair follicle approximating means that causes hair follicles of body hairs at the target site to approach the skin surface, thereby enhancing the irradiation efficiency of modulating light irradiated to the hair follicles.

1 Claim, 5 Drawing Sheets

FOREIGN PATENT DOCUMENTS

| | | |
|---|---|---|
| JP | 2001-292285 A | 10/2001 |
| JP | 2002-360336 A | 12/2002 |
| JP | 2004-141327 A | 5/2004 |
| JP | 2004-527330 | 9/2004 |
| JP | 2005-312599 A | 11/2005 |
| JP | 2006-289098 A | 10/2006 |
| WO | WO-95/33600 A1 | 12/1995 |
| WO | WO-96/23447 A1 | 8/1996 |
| WO | WO-99/34867 A1 | 7/1999 |
| WO | WO-02/094116 A1 | 11/2002 |

OTHER PUBLICATIONS

Korean Office Action for the Application No. 10-2009-7015730 from Korean Intellectual Property Office dated Apr. 28, 2011.

International Search Report for the Application No. PCT/JP2008/050983 mailed Mar. 18, 2008.

* cited by examiner (A)

(B)

HAIR GROWTH MODULATION DEVICE

TECHNICAL FIELD

The present invention relates to a hair growth modulation device for promoting or inhibiting body hair growth (including scalp hair) by irradiating light.

BACKGROUND ART

Although hair is known to be removed by laser light by using a hair growth modulation device using light as described in Japanese Patent Application Laid-open No. 2001-292285, attention is currently being focused on modulation of the growth of body hair with light having a quantity of light or luminous energy that does not cause changes in cell morphology as observed with existing therapeutic lasers.

Although body hair has a hair cycle during which hair changes in cycles consisting of a growth period, a regressive period and a rest period, when light, having a quantity of light or luminous energy that does not cause changes in cell morphology as observed with existing therapeutic lasers, is irradiated during the above-mentioned rest period, together with growth of hair during the growth period of the hair cycle proceeding rapidly, the absence of the occurrence of cell damage as well as the absence of the occurrence of adverse side effects such as burns has also been confirmed. In addition, when hair is irradiated with light of the above-mentioned quantity of light or luminous energy during the growth period of the hair cycle, hair growth has been confirmed to be effectively inhibited.

Furthermore, although the reason why scalp hair growth is promoted or inhibited when the hair is irradiated with light at a level that does not cause changes in cell morphology during the rest period or growth period is not clear, based on the results of analyses at the RNA level, activation of inflammatory cytokines is thought to occur as a result of the light irradiation, and the resulting promotion or inhibition of hair growth is thought to be the result of this activation of inflammatory cytokines.

However, in promoting or inhibiting hair growth by irradiating light for modulating hair growth as described above to human skin, it is only required to radiate light of a suitable light quantity without having luminous energy in the manner of a laser in order to modulate hair growth, and for this reason a xenon flash lamp is used for the light source. However, if it were possible to lower the required quantity of light even further, optical modulation of hair growth is expected to become more appealing since it would be possible to use other light sources that are inexpensive and easy to use.

DISCLOSURE OF THE INVENTION

With the foregoing in view, an object of the present invention is to provide a hair growth modulation device capable of reducing the quantity of light required by modulating light for modulating growth of body hair.

The hair growth modulation device as claimed in the present invention is provided with a light irradiator for irradiating modulating light for modulating body hair growth to a target site of a human body, and a hair follicle approximating means for approximating hair follicles of body hairs at the target site towards the light irradiator when the modulating light is irradiated to the target site. As a result of approximating body hair to be irradiated with light towards the skin surface, the quantity of light that reaches the follicles increases. As a result, high light irradiation efficiency sufficient for the quantity of light irradiated to the hair follicles can be maintained while being able to lower the capacity required by the light irradiator, thereby making it possible to use a light source having a low radiated quantity of light for the light irradiator.

A mechanical shaving means for shaving body hair, a mechanical epilating means for epilating body hair, or a suction means for suctioning the skin surface can be preferably used for the hair follicle approximating means.

Moreover, an abrasive means configured so as to approximate hair follicles towards the skin surface by scraping the skin surface at the target site can also be used for the hair follicle approximating means. In this case, the reflectance of light at the target site can be lowered by scraping the skin surface and making it smooth, thereby enhancing the irradiation efficiency of the modulating light and as a result, making it possible to further lower the quantity of light required by the light source.

BRIEF DESCRIPTION OF THE DRAWINGS

FIG. 2(A) is a perspective view of a hair growth modulation device as claimed in a second embodiment of the present invention, while FIG. 2(B) is a partial side view of the same;

BEST MODE FOR CARRYING OUT THE INVENTION

Figure 1:
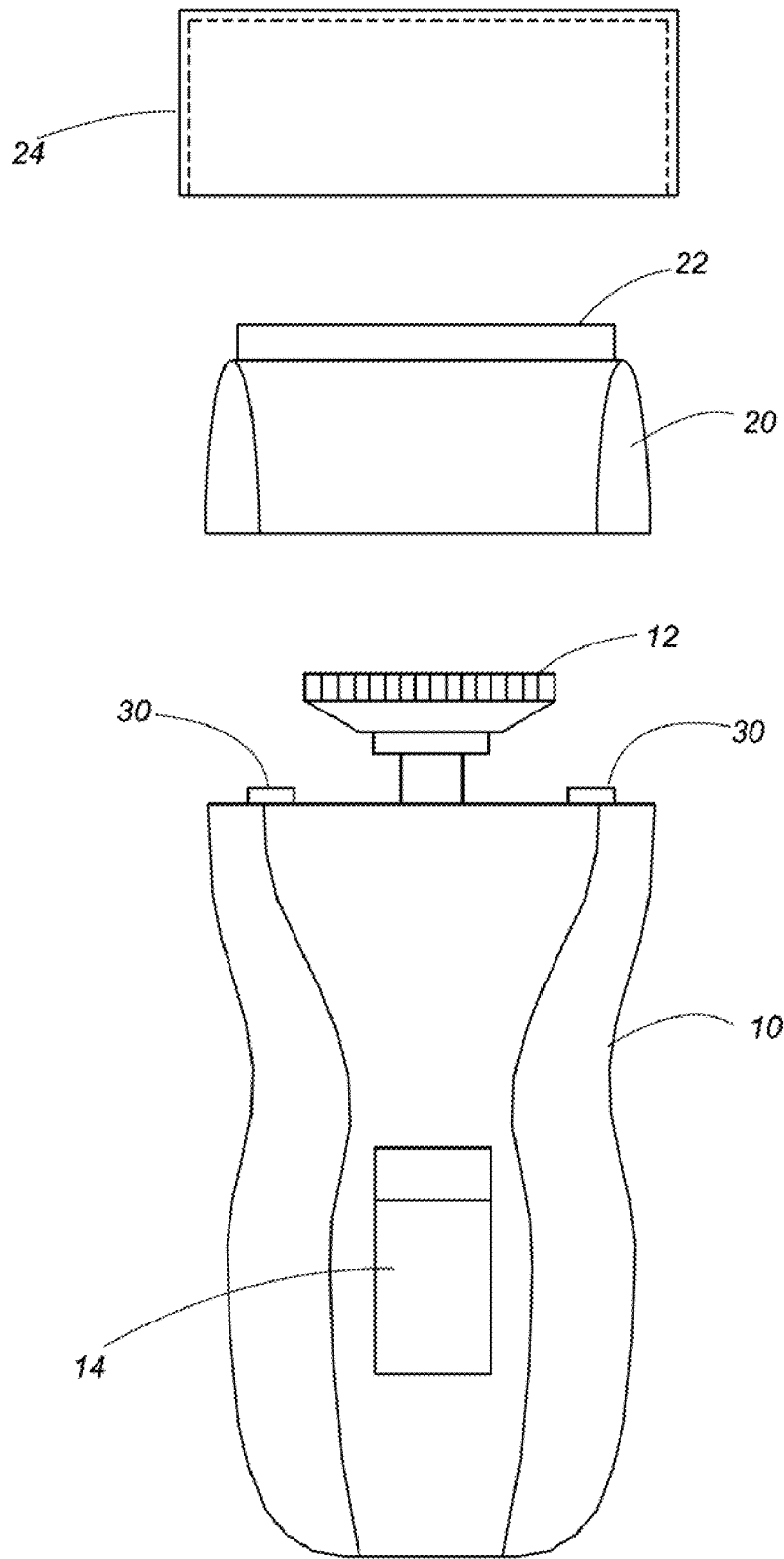
FIG. 1 is an exploded front view of a hair growth modulation device as claimed in a first embodiment of the present invention.

The following provides an explanation of the present invention based on embodiments shown in the appended drawings. FIG. 1 shows a hair growth modulation device as claimed in a first embodiment of the present invention. This device is provided with a grip 10 provided with a shaving head 20 on the upper end thereof, light irradiators 30 for irradiating modulating light for modulating growth of body hair are formed on the upper end of the grip 10, and the modulating light is irradiated onto skin of the body through the shaving head 20. These light irradiators 30 use a xenon flash lamp for the light source, and output modulating light in the form of flashing light having a wavelength of 400 to 600 nm to a target site on skin of the body in order to modulate growth of body hair. Consequently, the light irradiators 30 are provided with a drive circuit, for driving the xenon flash lamp and causing the xenon flash lamp to continuously emit modulating light in a short period of time of 1 ms or less, and a filter.

The shaving head 20 holds an outer blade 22 having a plurality of blade holes, and shaves hair as a result of an inner blade 12 protruding from the upper end of the grip 10 moving while making sliding contact with the outer blade 22. The inner blade 12 is driven to reciprocate or rotate by a motor (not shown) housed within the grip 10.

The light irradiators 30 are arranged on both sides of the inner blade 12, and a lens (not shown) is provided for collecting modulating light towards the vicinity of the portions of the inner blade 12 and the outer blade 22 making contact, and modulating light output through the lens is irradiated to the skin through the blade holes of the outer blade 22.

A removable cap 24 is provided on the shaving head 20. This cap is formed from a light-blocking material. This cap is made from a light-blocking material. In a case where the cap is attached to the shaving head, this cap is shaped to prevent modulating light which escapes to the outside from the light irradiator.

A switch 14 arranged on the grip 10 operates the motor for driving the inner blade 12 and the light irradiator 30, and modulating light output from the light irradiator 30 is irradiated to the skin through the blade holes of the outer blade 22 during the operation of shaving body hair.

When cutting body hairs between the outer blade 22 and the inner blade 12, since body hairs are cut while being pulled in the direction of movement of the inner blade 12 as a result of skin entering the blade holes of the outer blade 22, hair follicles of the body hairs are pulled up to the skin surface, and modulating light is irradiated to hair follicles that have approached the skin surface. Thus, even if the quantity of modulating light output from the light irradiator 30 is equal, the quantity of light received by the hair follicles increases in the case the locations of the hair follicles irradiated with light are closer to the skin surface. Thus, in order to maintain a quantity of light required for modulating hair growth for the quantity of light to be irradiated to the hair follicles, the light irradiator 30 can be used at a lower output in the case a hair shaving means composed of the outer blade 22 and the inner blade 12 is present as compared with the case in which it is not present.

Figure 2:
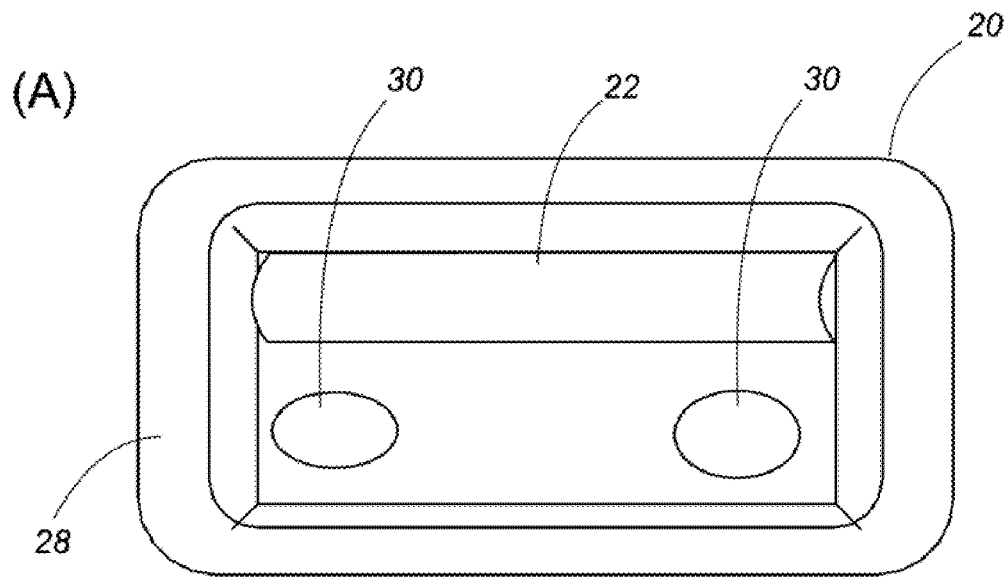
Figure 2:
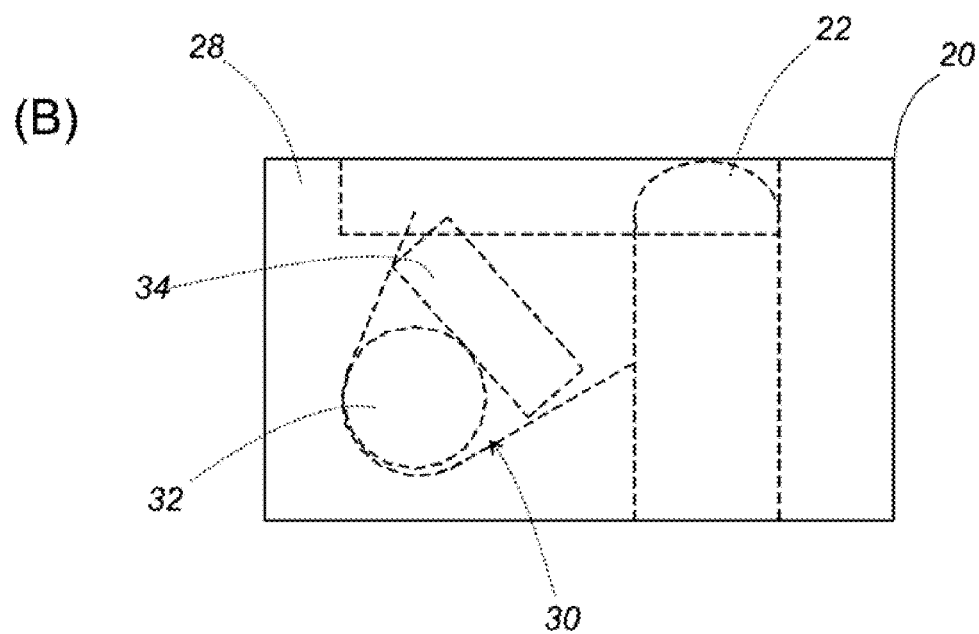

FIG. 2 shows a hair growth modulation device as claimed in a second embodiment of the present invention. Although this device is also provided with a shaving head 20 in the same manner as in the above-mentioned first embodiment, the light irradiators 30 are arranged outside of the outer blade 22 in the shaving head 20. The light irradiators 30 are provided with a light source 32 and a condenser lens 34, and modulating light is irradiated towards the apex of the outer surface (surface contacting the skin) of the outer blade 22. In this case, modulating light from the light irradiators 30 is irradiated to the skin pushed against the outer blade 22 without being blocked by the outer blade 22. A peripheral wall 28 surrounding the outer blade 22 and the light irradiators 30 protrudes from the periphery of the shaving head 20, and reduces the escape of modulating light to the outside.

Figure 3:
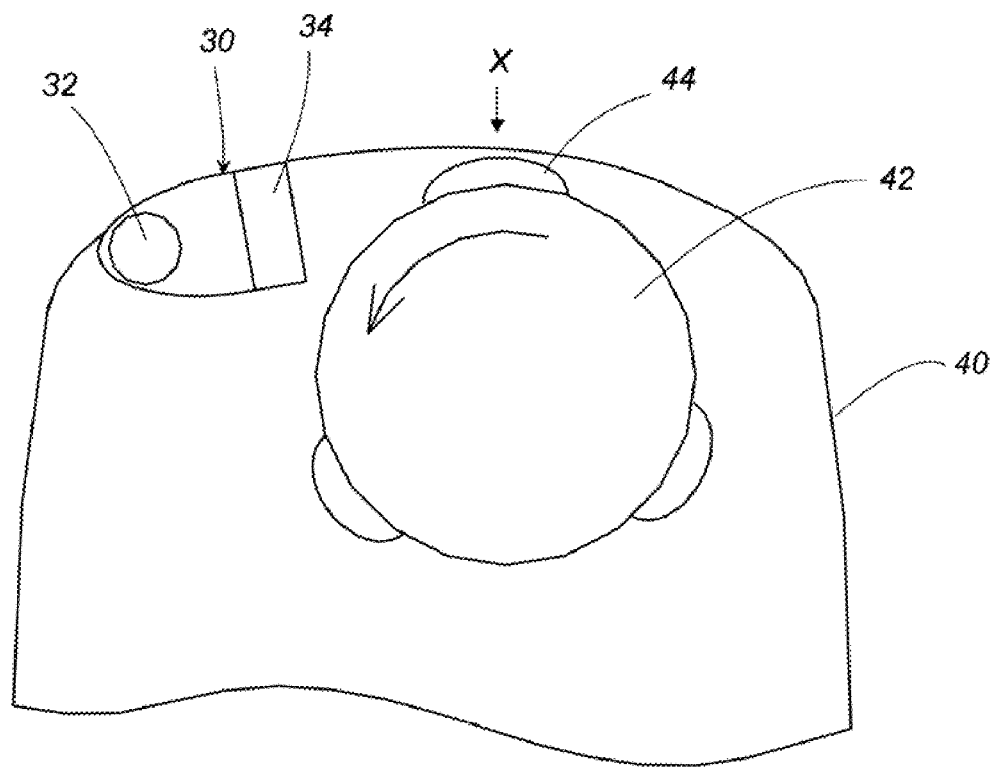
FIG. 3 is a cross-sectional view of a hair growth modulation device as claimed in a third embodiment of the present invention.

FIG. 3 shows a hair growth modulation device as claimed in a third embodiment of the present invention. This device is similar to the first embodiment with the exception of using an epilating head 40 instead of the shaving head 20. The epilating head 40 is provided with a rotating cylinder 42 on which is arranged a plurality of pinching claws 44. The pinching claws 44 are arranged in a row along the axial direction of the rotating cylinder 42. According to movement of pinching claws 44 in the axial direction, the pinching claws 44 are configured to pinch body hairs in a condition where the pinching claws 44 are closed, and are configured to release the body hairs in a condition where the pinching claws 44 are opened. The rotating cylinder is driven to rotate in the direction indicated by the arrow in the drawing by a motor (not shown), the pinching claws 44 open and close accompanying this rotation, body hairs are pinched as a result of the claws 44 closing in the vicinity of the location of X in the drawing, body hairs are epilated as a result of the rotating cylinder 42 continuing to rotate in the direction of the arrow, and the epilated body hairs are subsequently released when the pinching claws 44 open.

In the present embodiment, the light irradiators 30 are provided with a light source 32 and a condenser lens 34, are located to the side of the rotating cylinder 40 and in the direction in which the pinching claws 44 epilate body hairs, and irradiate light onto hair follicles that have been pulled up towards the skin surface as a result of being pulled by the pinching claws 44.

Figure 4:
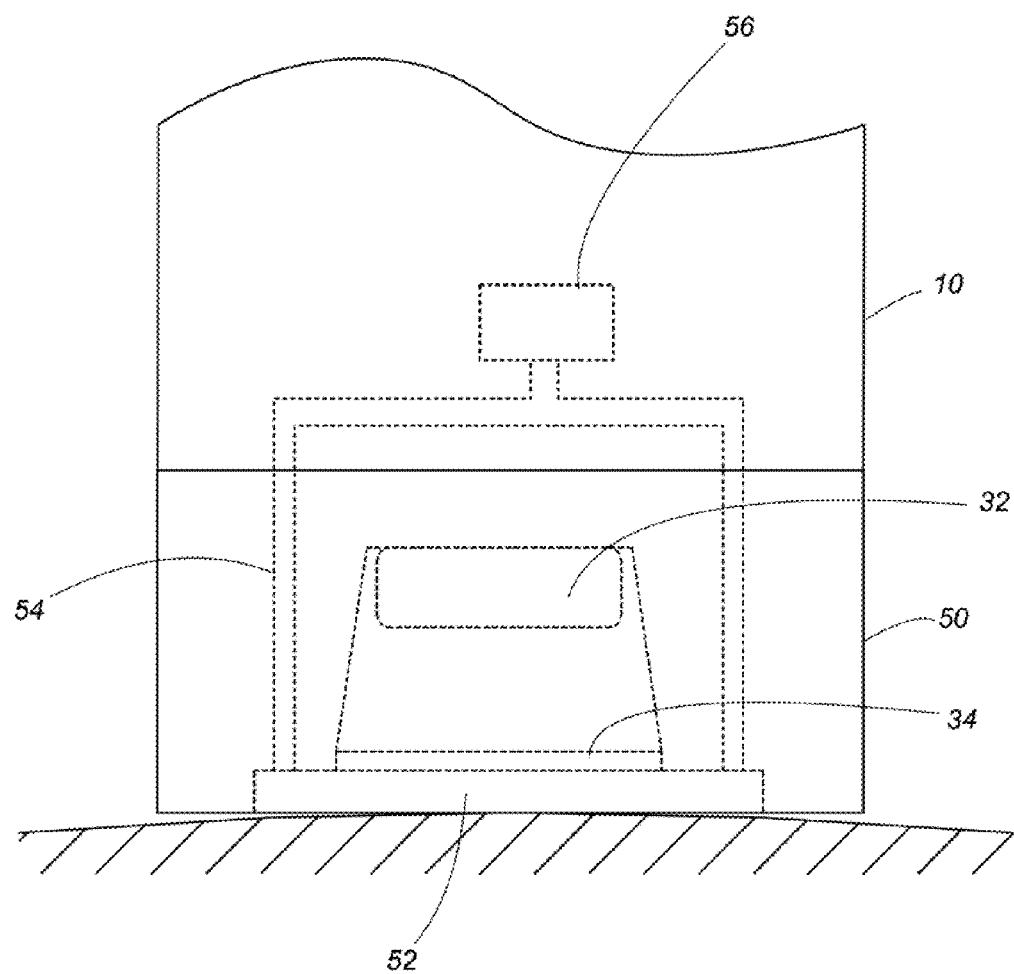
FIG. 4 is a cross-sectional view of a hair growth modulation device as claimed in a fourth embodiment of the present invention.

FIG. 4 shows a hair growth modulation device as claimed in a fourth embodiment of the present invention. This device uses a suction head 50 instead of a shaving head, while other constituents are the same as those of the first embodiment. A recess 52 is formed on the leading end surface of the suction head 50 that serves as a contact surface with the skin, the lens 34 of the light irradiators 30 is arranged on the bottom wall of this recess 52, and the skin is irradiated by modulating light from the light source 32 within the suction head 50 through the lens 34. A portion of the bottom wall of the recess 52 is connected to a suction pump 56 provided within the grip 10 through a suction pathway 54, and a portion of the skin is pulled into the recess 52 by suctioning a portion of the skin in contact with the leading end surface of the suction head 50. Accompanying this, body hairs and hair follicles are pulled towards the light source 32 and as a result thereof, modulating light from the light irradiators 30 is efficiently radiated to the hair follicles. The hair growth modulation device as claimed in this embodiment is particularly effective in the case of promoting the growth of body hair.

Figure 5:
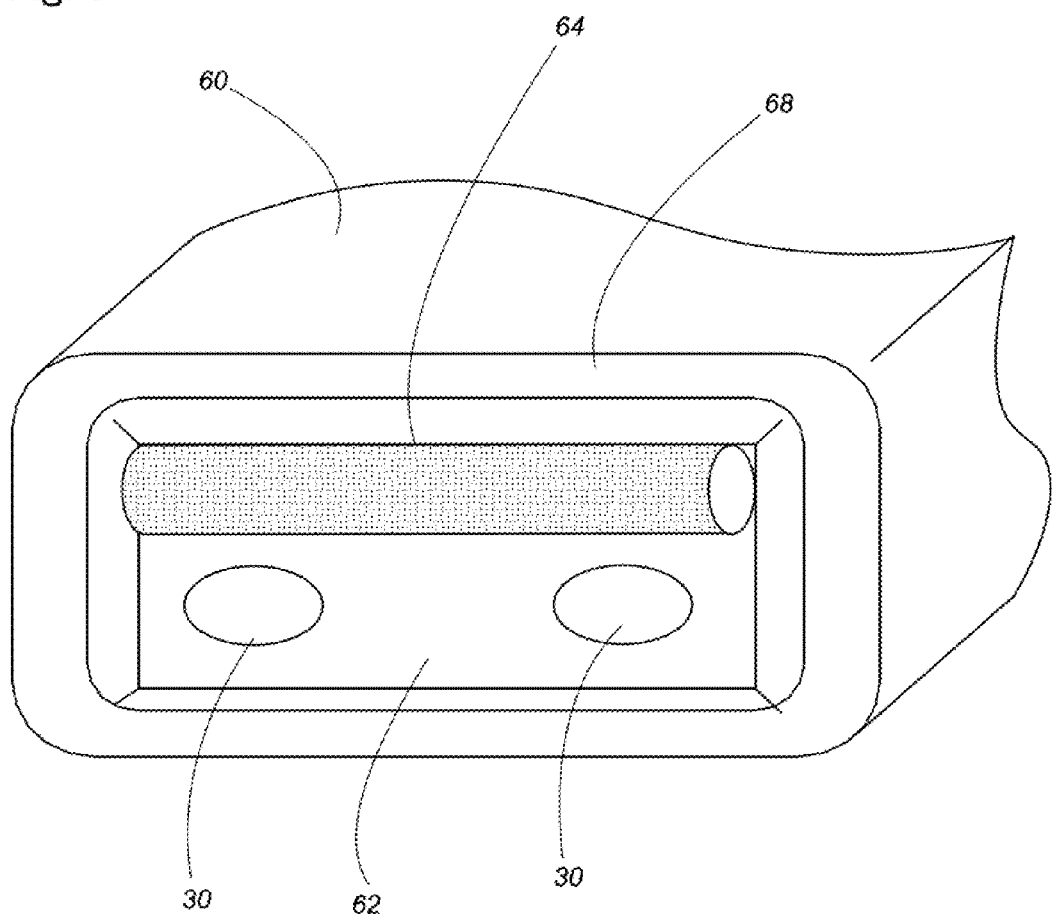
FIG. 5 is a partial perspective view of a hair growth modulation device as claimed in a fifth embodiment of the present invention.

FIG. 5 shows a hair growth modulation device as claimed in a fifth embodiment of the present invention. This device uses a head 60 provided with an abrasive roller 64 instead of a shaving head, while other constituents are the same as those of the first embodiment. The abrasive roller 64 is retained within a recess 62 formed in the leading end surface of the head 60 and is able to rotate about the axis thereof, and causes hair follicles to approach the skin surface, namely the light irradiators 30, by scraping the old horny layer of the skin surface. As a result, the irradiation efficiency of light onto the hair follicles can be enhanced. In addition, although the old horny layer of the skin surface lowers light transmittance by absorbing light in addition to having high light reflectance, light reflectance can be reduced by removing the old horny layer prior to irradiating modulating light from the light irradiators 30, thereby making it possible to increase the quantity of light reaching the roots of body hairs. Moreover, the present embodiment can also be configured so as to connect a suction pump (not shown) to the recess 62 as indicated in the fourth embodiment. In this case, skin can be suctioned within the recess 62 while removing the removed horny layer by pressing the peripheral wall 68 surrounding the recess 62 against the skin, thereby enabling hair follicles to get even closer to the light irradiators 30 and further enhancing irradiation efficiency of the modulating light. The abrasive roller 64 may also be driven to rotate by a motor. Although the abrasive roller is disclosed as an example of a scraping means for removing the horny layer by scraping the surface of the skin, the present invention is not necessarily limited thereto, but rather another scraping means can also be used that demonstrates a similar function.

Furthermore, although the above-mentioned embodiments indicate the use of a xenon flash lamp as a light source for the light irradiators 30, that which outputs laser light may be used, or a lamp having an output lower than that of a xenon flash lamp may also be used.

The invention claimed is:

1. A hair growth modulation device comprising:
   a light irradiator configured to continuously irradiate a modulating light having energy not causing changes in cell morphology in a short period of 1 ms or less for modulating hair growth to a target site of a human body, said modulating light having a wavelength of 400 nm to 600 nm;

a hair follicle approximating means configured to approximate hair follicles of body hairs at the target site towards said light irradiator when said modulating light is irradiated, wherein said hair follicle approximating means is a mechanical shaving means for shaving the body hairs, and wherein said mechanical shaving means is provided with a head which is pushed to the target site of the human body, wherein said head is provided with an outer blade having a plurality of blade holes and an inner blade slidably contacting said outer blade, and wherein said light irradiator is arranged outside of said outer blade so as to irradiate the modulating light towards an outer surface of said outer blade.

* * * * *